(12) United States Patent
Nauwelaers et al.

(10) Patent No.: US 10,533,210 B2
(45) Date of Patent: Jan. 14, 2020

(54) DETECTION OF METHYLATED DNA (71) Applicant: Biocartis NV, Mechelen (BE)

(72) Inventors: David Nauwelaers, Kortrijk-Dutsel (BE); Hannah Kenens, Kessel (BE)

(73) Assignee: Biocartis NV, Mechelen (BE)

(*) Notice: Subject to any disclaimer, the term of this patent is extended or adjusted under 35 U.S.C. 154(b) by 0 days.

(21) Appl. No.: 15/570,946

(22) PCT Filed: Jun. 10, 2016

(86) PCT No.: PCT/EP2016/063269
§ 371 (c)(1),
(2) Date: Oct. 31, 2017

(87) PCT Pub. No.: WO2016/198582
PCT Pub. Date: Dec. 15, 2016

(65) Prior Publication Data
US 2018/0201973 A1 Jul. 19, 2018

(30) Foreign Application Priority Data

Jun. 10, 2015 (EP) .................................... 15171523

(51) Int. Cl.
*C12Q 1/6806* (2018.01)
*C12Q 1/6827* (2018.01)

(52) U.S. Cl.
CPC ......... *C12Q 1/6806* (2013.01); *C12Q 1/6827* (2013.01); *C12Q 2523/125* (2013.01); *C12Q 2527/101* (2013.01)

(58) Field of Classification Search
None
See application file for complete search history.

(56) References Cited

U.S. PATENT DOCUMENTS

| 2005/0112658 A1 | 5/2005 | Makino |
| 2008/0220418 A1* | 9/2008 | Ballhause .......... C12N 15/1003 435/6.14 |
| 2015/0086972 A1 | 3/2015 | Millar |

FOREIGN PATENT DOCUMENTS

| JP | 2005-058217 | 3/2005 | |
| WO | 2007068437 A1 | 6/2007 | |
| WO | 2011036609 A1 | 3/2011 | |
| WO | WO-2013033749 A1 * | 3/2013 | .......... C12Q 1/6806 |
| WO | 2014128129 A1 | 8/2014 | |

OTHER PUBLICATIONS

Bailey, V.J., et al., "Single-Tube Analysis of DNA Methylation with Silica Superparamagnetic Beads", Clinical Chemistry, vol. 56, No. 6, Jun. 2010, pp. 1022-1025.
Holmes, Emily Eva, et al., "Performance Evaluation of Kits for Bisulfite-Conversion of DNA from Tissues, Cell Lines, FFPE Tissues, Aspirates, Lavages, Effusions, Plasma, Serum, and Urine", PLOS One, vol. 9, No. 4, Apr. 2014, p. e93933.
Shin, D.J., et al., "Droplet Bisulfite Conversion Platform for Epigenetic Cancer Biomarker Detection", Transducers & Eurosensors XXVII, IEEE, Jun. 2013, pp. 2181-2184.
International Search Report for PCT/EP2016/063269 dated Oct. 12, 2016.
Written Opinion for PCT/EP2016/063269 dated Oct. 12, 2016.
Japanese Office Action dated May 7, 2019 for Japanese Patent Application No. 2017-563560.

* cited by examiner

*Primary Examiner* — Joseph G. Dauner
(74) *Attorney, Agent, or Firm* — Quarles & Brady LLP (57) ABSTRACT

The present invention is based on the discovery of sensitive and specific methylation detection by a) controlling excessive DNA degradation prior to conversion by incubating DNA conversion reagent (e.g. bisulfite reagent) directly with a nucleic acid containing sample without requiring prior nucleic acid purification from the sample and without requiring prior nucleic acid denaturation at elevated temperatures of 98° C. and, b) optimizing bisulfite removal by controlling the pumping rate flow of the bisulfite treated sample over an extraction membrane inside an automated system.

7 Claims, 3 Drawing Sheets

Specification includes a Sequence Listing.

```
                            SEQUENCE LISTING

<160> NUMBER OF SEQ ID NOS: 6

<210> SEQ ID NO 1
<211> LENGTH: 68
<212> TYPE: DNA
<213> ORGANISM: Artificial
<220> FEATURE:
<223> OTHER INFORMATION: Artificial sequence created to test bisulfite
      conversion and detection of un-methylated cytosines and methylated
      cytosines

<400> SEQUENCE: 1
tctcccatcc cctcccacaa accaccaatc ctccccacaa tcaccaaaca cacacaatca      60
acacccac                                                              68

<210> SEQ ID NO 2
<211> LENGTH: 68
<212> TYPE: DNA
<213> ORGANISM: Artificial
<220> FEATURE:
<223> OTHER INFORMATION: Artificial sequence created to test bisulfite
      conversion and detection of un-methylated cytosines and methylated
      cytosines

<400> SEQUENCE: 2
agagggtagg ggagggtgtt tggtggttag gagggtgtt agtggtttgt gtgtgttagt      60
tgtgggtg                                                              68

<210> SEQ ID NO 3
<211> LENGTH: 68
<212> TYPE: DNA
<213> ORGANISM: Artificial
<220> FEATURE:
<223> OTHER INFORMATION: Artificial sequence created to test bisulfite
      conversion and detection of un-methylated cytosines and methylated
      cytosines

<400> SEQUENCE: 3
agagggcagg ggagggcgcc tggcggttag gagggcgct agcggtttgc gcgtgttagt      60
tgcgggcg                                                              68

<210> SEQ ID NO 4
<211> LENGTH: 68
<212> TYPE: DNA
<213> ORGANISM: Artificial
<220> FEATURE:
<223> OTHER INFORMATION: Artificial sequence created to test bisulfite
      conversion and detection of un-methylated cytosines and methylated
      cytosines

<400> SEQUENCE: 4
tctcccgtcc cctcccgcgg accgccaatc ctccccgcga tcgccaaacg cgcacaatca     60
acgcccgc                                                             68

<210> SEQ ID NO 5
<211> LENGTH: 68
<212> TYPE: DNA
<213> ORGANISM: Artificial
<220> FEATURE:
<223> OTHER INFORMATION: Artificial sequence created to test bisulfite
      conversion and detection of un-methylated cytosines and methylated
```

```
        cytosines

<400> SEQUENCE: 5
agagggcagg ggagggcgcc tggcggttag gaggggcgct agcggtttgc gcgtgttagt     60
tgcgggcg                                                             68

<210> SEQ ID NO 6
<211> LENGTH: 68
<212> TYPE: DNA
<213> ORGANISM: Artificial
<220> FEATURE:
<223> OTHER INFORMATION: Artificial sequence created to test bisulfite
      conversion and detection of un-methylated cytosines and methylated
      cytosines

<400> SEQUENCE: 6
agagggcagg ggagggcgcc tggcggttag gaggggcgct agcggtttgc gcgtgttagt     60
tgcgggcg                                                             68
```

DETECTION OF METHYLATED DNA

CROSS-REFERENCE TO RELATED PATENT APPLICATIONS

The present application is the U.S. national phase application of International Application No. PCT/EP2016/063269, filed on Jun. 10, 2016, which application claims the benefit of priority to European Patent Application No. 15171523.2, filed on Jun. 10, 2015, the contents of which are incorporated herein by reference in their entireties.

FIELD OF THE INVENTION

The present application relates to methods of detection of methylated cytosines in nucleic acids on an automated system, and to uses of said system and cartridges for said system for the detection and analysis of methylated nucleic acids.

INTRODUCTION

DNA methylation is one of the mechanisms for the epigenetic control of gene expression. Alterations in the methylation status of genomic DNA can result in the silencing of genes. Such control is of significance for a wide range of biological processes, including cellular proliferation e.g. via transcriptional silencing of critical growth regulators such as tumor suppressor genes. The biological significance of DNA methylation in the regulation of gene expression and its role in cancer is increasingly recognized. DNA methylation occurs by covalent addition of a methyl group at the 5' carbon of the cytosine ring, converting the cytosine in the genomic DNA to 5-methylcytosine. In mammalian DNA, 5-methylcytosine is found in approximately 4% of genomic DNA, primarily at sequence strands enriched in cytosine-guanosine dinucleotides (CpGs), so called "CpG islands". The hypermethylation of some CpG islands in genomic DNA could result in gene silencing and hypomethylation can lead to transcription and gene expression.

There has been a great interest in developing molecular techniques to analyse genomic DNA methylation at the CpG islands. The discovery that DNA treatment with sodium bisulfite converts the cytosine to uracil while keeping the 5-methycytosine intact has opened the door to a number of strategies to investigate genomic DNA methylation both at regional and global levels (Frommer et al.). Typically, the process involves the basic steps of:

1) DNA purification from a sample,
2) DNA denaturation (DNA heating step at 98° C. for at least 10 min),
3) deamination with sulphonation via incubation of the DNA with bisulfite (conversion reagent) at an elevated temperature (1 hour or more at at least 54° C.) to produce converted DNA,
4) removal of the bisulfite by purification, usually over a column with a DNA binding medium (a resin or a membrane),
5) desulphonation, i.e. addition of desulphonation buffer, followed by incubation for usually 20 min. at room temperature, and removal of the desulphonation buffer by centrifugation,
6) one or more washing steps,
7) elution of the DNA, usually by addition of an elution buffer and a centrifugation step (on a column).

DNA methylation detection is currently prominently applied in disease diagnosis methods. In particular, such methods can be applied in cancer diagnostics.

To effectively and efficiently prepare converted DNA for use in various downstream analyses, an ideal DNA bisulfite modification method should be: (1) highly accurate to allow complete conversion of cytosine to uracil without deamination of methylcytosine to thymine; (2) conservative enough to minimise DNA degradation and (3) as rapid as possible to enable the bisulfite process to be as short as possible. Unfortunately, most of the current DNA conversions methods show large variations due to insufficient control of manual handlings and bisulfite incubation time that is a key consideration for successful bisulfite conversion.

A further limitation of many current commercially available kits is that they usually include a bisulfite removal step after the conversion and before further downstream analysis of the sample can take place. This inevitably introduces additional manual handling steps such as addition of several buffers including washing buffers and elution buffers, performing additional centrifugation steps, running the sample over low-elution spin columns, etc. Additionally, given the fact that many of the currently available kits require preparation of the patient sample beforehand, e.g. DNA purification and/or DNA denaturation in a heating step, the existing DNA bisulfite modification methods involve a lot of manual handling, which makes them difficult to automate and also time-consuming.

The factors as described are limiting optimal DNA bisulfite conversion and further make it a time-consuming process that is to be performed by trained lab personnel. Accordingly, there appears to be a need for a methylated DNA detection system that provides a solution to the problems posed.

SUMMARY OF THE INVENTION

The invention as set out in the claims, is based on the discovery of sensitive and specific methylation detection by a) controlling excessive DNA degradation prior to conversion by incubating DNA conversion reagent (e.g. bisulfite reagent) directly with a nucleic acid containing sample without requiring prior nucleic acid purification from the sample and without requiring prior nucleic acid denaturation at elevated temperatures of 98° C. and, b) optimizing bisulfite removal by controlling the pumping rate flow of the bisulfite treated sample over an extraction membrane inside an automated system.

Accordingly, the invention provides in a first aspect a method for a detection of a nucleic acid methylation status in an automated system comprising an extraction chamber comprising an extraction membrane, said method comprising the steps of:
  introducing a source of the nucleic acid into the automated system, adding bisulfite to the nucleic acid and immediately followed by heating the source of the nucleic acid to produce a lysate comprising the nucleic acid and to deaminate an unmethylated cytosine base present in said nucleic acid;
  adding binding buffer to the lysate to produce a binding buffer-and-lysate-solution;
  binding the nucleic acid to the extraction membrane and removing the bisulfite by transporting the binding buffer-and-lysate-solution over the extraction membrane;
  adding desulphonation buffer to the extraction chamber and transporting the desulphonation buffer over the extraction membrane to desulphonate the base deaminated in a previous step in the nucleic acid and to convert said base to an uracil base, eluting the converted nucleic acid from the extraction membrane; and analyzing the converted nucleic acid.

In a more specific aspect, a method is provided for a detection of a nucleic acid methylation status in an automated system comprising an extraction chamber comprising an extraction membrane, said method comprising the steps of:

introducing a source of the nucleic acid into the automated system, adding bisulfite to the nucleic acid and immediately followed by heating the source of the nucleic acid to a temperature between 40° C. and 80° C. to produce a lysate comprising the nucleic acid and to deaminate an unmethylated cytosine base present in said nucleic acid;

adding binding buffer to the lysate to produce a binding buffer-and-lysate-solution;

binding the nucleic acid to the extraction membrane and removing the bisulfite by controlled pumping of the binding buffer-and-lysate-solution over the extraction membrane;

adding desulphonation buffer to the extraction chamber and controlled pumping of the desulphonation buffer over the extraction membrane to desulphonate the base deaminated in a previous step in the nucleic acid and to convert said base to an uracil base, eluting the converted nucleic acid from the extraction membrane; and analyzing the converted nucleic acid in the automated system.

In a more specific aspect, a method is provided for a detection of a nucleic acid methylation status in an automated system comprising an extraction chamber comprising an extraction membrane, said method comprising the steps of:

introducing a source of the nucleic acid into the automated system, adding bisulfite to the nucleic acid and immediately followed by heating the source of the nucleic acid to a temperature between 40° C. and 60° C. to produce a lysate comprising the nucleic acid and to deaminate an unmethylated cytosine base present in said nucleic acid;

adding binding buffer to the lysate to produce a binding buffer-and-lysate-solution;

binding the nucleic acid to the extraction membrane and removing the bisulfite by pumping the binding buffer-and-lysate-solution over the extraction membrane with a flow rate slower than or equal to 0.1 ml/s;

adding desulphonation buffer to the extraction chamber and pumping the desulphonation buffer over the extraction membrane with a flow rate slower than or equal to 0.1 ml/s to desulphonate the base deaminated in the first step in the nucleic acid and to convert said base to an uracil base;

eluting the converted nucleic acid from the extraction membrane; and analyzing the converted nucleic acid in the automated system.

The methods of the invention can be applied in a cartridge, which itself can be loaded into an automated system. Thus, in a further aspect use of a cartridge is provided for detection of a nucleic acid methylation status, the cartridge comprising:

a lysis chamber susceptible of receiving a source of the nucleic acid, adding bisulfite solution to the source of the nucleic acid and immediately followed by heating the source of the nucleic acid to a temperature between 40° C. and 80° C. to produce a lysate comprising the nucleic acid and to deaminate an unmethylated cytosine base present in said nucleic acid, and adding binding buffer to the converted lysate to form a binding buffer-and-lysate-solution, an extraction chamber comprising an extraction membrane susceptible of receiving the binding buffer-and-lysate-solution, allowing subsequent removal of the bisulfite by controlled pumping of the binding buffer-and-lysate-solution over the extraction membrane, allowing subsequent addition of desulphonation buffer to the extraction chamber and controlled pumping of the desulphonation buffer over the extraction membrane to perform alkali desulphonation of the base deaminated in the first step in the nucleic acid and to convert said base to an uracil base, and allowing subsequent elution of the converted nucleic acid from the extraction membrane, wherein there is a channel between the lysis chamber and the extraction chamber for transporting fluids from the lysis chamber to the extraction chamber, and, a PCR chamber allowing downstream analysis of the converted nucleic acid, wherein there is a channel between the extraction chamber and the PCR chamber for transporting converted nucleic acid from the extraction chamber to the PCR chamber.

In a more specific aspect, the use of a cartridge is provided for detection of a nucleic acid methylation status, the cartridge comprising:

a lysis chamber susceptible of receiving a source of the nucleic acid, adding bisulfite solution to the source of the nucleic acid and immediately followed by heating the source of the nucleic acid to a temperature between 40° C. and 60° C. to produce a lysate comprising the nucleic acid and to deaminate an unmethylated cytosine base present in said nucleic acid, and adding binding buffer to the converted lysate to form a binding buffer-and-lysate-solution, an extraction chamber comprising an extraction membrane susceptible of receiving the binding buffer-and-lysate-solution, allowing subsequent removal of the bisulfite by pumping the binding buffer-and-lysate-solution over the extraction membrane with a flow rate slower than or equal to 0.1 ml/s, allowing subsequent addition of desulphonation buffer to the extraction chamber and pumping the desulphonation buffer over the extraction membrane with a flow rate slower than or equal to 0.1 ml/s to perform alkali desulphonation of the base deaminated in the first step in the nucleic acid and to convert said base to an uracil base, and allowing subsequent elution of the converted nucleic acid from the extraction membrane, wherein there is a channel between the lysis chamber and the extraction chamber for transporting fluids from the lysis chamber to the extraction chamber, and, a PCR chamber allowing downstream analysis of the converted nucleic acid, wherein there is a channel between the extraction chamber and the PCR chamber for transporting converted nucleic acid from the extraction chamber to the PCR chamber.

In a next aspect of the invention, use of an automated system is provided for a detection of a nucleic acid methylation status in a source of a nucleic acid, the automated system adapted for receiving a cartridge according to the invention, the system controlling the steps of:
  adding bisulfite to a source of a nucleic acid introduced into the system and immediately followed by heating the source of the nucleic acid to a temperature between 40° C. and 80° C. to produce a lysate comprising the nucleic acid and to deaminate an unmethylated cytosine base present in said nucleic acid,
  adding binding buffer to the lysate comprising nucleic acid to produce a binding buffer-and-lysate-solution,
  binding the nucleic acid to the extraction membrane and removing the bisulfite by controlled pumping of the binding buffer-and-lysate-solution over the extraction membrane,
  adding desulphonation buffer to the extraction chamber and controlled pumping of the desulphonation buffer over the extraction membrane to desulphonate the base deaminated in a previous step in the nucleic acid and to convert said base to an uracil base,
  eluting the converted nucleic acid from the extraction membrane, and
  analyzing the converted nucleic acid.

In a more specific aspect of the invention, use of an automated system is provided for a detection of a nucleic acid methylation status in a source of a nucleic acid, the automated system adapted for receiving a cartridge as defined throughout this application, the system controlling the steps of:
  adding bisulfite to a source of a nucleic acid introduced into the automated system and immediately followed by heating the source of the nucleic acid to a temperature between 40° C. and 60° C. to produce a lysate comprising the nucleic acid and to deaminate an unmethylated cytosine base present in said nucleic acid,
  adding binding buffer to the lysate comprising nucleic acid to produce a binding buffer-and-lysate-solution,
  binding the nucleic acid to the extraction membrane and removing the bisulfite by pumping the binding buffer-and-lysate-solution over the extraction membrane with a flow rate slower than or equal to 0.1 ml/s,
  adding desulphonation buffer to the extraction chamber and pumping the desulphonation buffer over the extraction membrane with a flow rate slower than or equal to 0.1 ml/s to desulphonate the base deaminated in the first step in the nucleic acid and to convert said base to an uracil base,
  eluting the converted nucleic acid from the extraction membrane, and
  analyzing the converted nucleic acid.

It is also an aspect of the present invention to provide a kit for the detection of methylated DNA via bisulfite conversion of DNA in a sample, the kit comprising:
  a cartridge according to the invention for use in an automated system, comprising bisulfite, binding buffer and desulphonation buffer, and
  instructions for use.

The invention in all of its aspects and embodiments allows the automatization of the process by the omission of uncontrolled manual handlings performed by trained laboratory person and by using laboratory equipment. More particularly, the invention omits separate DNA purification, DNA denaturation, elution over columns and centrifuges, but instead all the steps required for bisulfite conversion of DNA in a sample are performed inside an automated system that controls all nucleic acid handling steps, including automated flow and timing steps.

DETAILED DESCRIPTION OF THE INVENTION

Generally, the methods of the invention are directed to analyzing the methylation status of one or more target nucleotides in one or more target sequences in a sample. The present invention facilitates the analysis of the methylation status of DNA in a patient sample. The invention provides in a first aspect a method for bisulfite conversion of DNA (in a sample) in an automated system containing an extraction membrane, whereby the treated sample is pumped over the extraction membrane in several automated pumping steps. By a combination of making the prior DNA purification and DNA denaturation in a patient sample obsolete, and by pumping the bisulfite treated sample over an extraction membrane inside the automated system, the efficacy and ease of use of the bisulfite conversion process is improved.

In one embodiment of the invention, a method is provided for a detection of a nucleic acid methylation status in an automated system comprising an extraction chamber comprising an extraction membrane, said method comprising the steps of, or characterized by:
  introducing a source of the nucleic acid into the automated system, adding bisulfite to the nucleic acid and immediately followed by heating the source of the nucleic acid to a temperature between 40° C. and 80° C. to produce a lysate comprising the nucleic acid and to deaminate an unmethylated cytosine base present in said nucleic acid;
  adding binding buffer to the lysate to produce a binding buffer-and-lysate-solution;
  binding the nucleic acid to the extraction membrane and removing the bisulfite by controlled pumping of the binding buffer-and-lysate-solution over the extraction membrane;
  adding desulphonation buffer to the extraction chamber and controlled pumping the desulphonation buffer over the extraction membrane to desulphonate the base deaminated in the first step in the nucleic acid and to convert said base to an uracil base;
  eluting the converted nucleic acid from the extraction membrane; and analyzing the converted nucleic acid in the automated system.

Alternatively, the converted nucleic acid can be analyzed in another automated system than the automated system which is used to perform the bisulfite conversion. After eluting the converted nucleic acid from the extraction membrane in an automatic system, the converted nucleic acid may be analyzed in another system, for example in a (DNA) sequencer.

In the context of the invention, the nucleic acid is genomic DNA that may comprise methylated-cytosine bases in CpG sites. Treating DNA with bisulfite (bisulfite conversion or bisulfite reaction) chemically modifies non-methylated cytosines into uracil, whilst (5-)methylated cytosines remain unchanged. The chemistry of (non-methylated) cytosine deamination by sodium bisulphite involves three steps: (1) sulphonation: the addition of bisulphite to the 5-6 double bond of cytosine, (2) hydrolic deamination: hydrolytic deamination of the resulting cytosine-bisulphite derivative to give a uracil-bisulphite derivative, (3) alkali desulphonation: removal of the sulphonate group by an alkali treatment, to give uracil. Once converted, the methylation profile of the DNA can be determined using the desired downstream application (subsequent amplification with primers specific for methylated versus unmethylated DNA). The term "converted DNA" and "converted nucleic acid" as used herein means "bisulfite treated DNA" and "bisulfite treated nucleic acid". Strictly considered, only the non-methylated cytosines in the DNA/nucleic acid will be chemically modified or converted into uracil by the bisulfite treatment, whilst the (5-) methylated cytosines will not be modified or converted by the bisulfite treatment. However, when DNA/nucleic acids have been treated with bisulfite, this is described as converted DNA/converted nucleic acid throughout the text.

In a related embodiment, an alternative method is provided for a detection of methylated DNA via bisulfite conversion of DNA in a sample in an automated system comprising an extraction chamber comprising an extraction membrane, said method comprising the steps of, or characterized by:

introducing a sample into the automated system, adding bisulfite to the sample and immediately heating the sample to a temperature between 40° C. and 80° C. to produce a lysate comprising DNA and to perform bisulfite conversion of the DNA;

adding binding buffer to the lysate comprising DNA to produce a binding buffer-and-lysate-solution;

binding the DNA to the extraction membrane and removing the bisulfite by controlled pumping the binding buffer-and-lysate-solution over the extraction membrane;

adding desulphonation buffer to the extraction chamber and controlled pumping the desulphonation buffer over the extraction membrane;

eluting the converted DNA from the extraction membrane; and analyzing the converted DNA in the automated system.

The invention also includes a method of preparing a sample for methylation analysis via bisulfite conversion of DNA in a sample in an automated system comprising an extraction chamber comprising an extraction membrane, said method comprising the steps of, or characterized by:

introducing a sample into the automated system, adding bisulfite to the sample and immediately heating the sample to a temperature between 40° C. and 80° C. to produce a lysate comprising DNA and to perform bisulfite conversion of the DNA;

adding binding buffer to the lysate comprising DNA to produce a binding buffer-and-lysate-solution;

binding the DNA to an extraction membrane and removing the bisulfite by controlled pumping the binding buffer-and-lysate-solution over the extraction membrane;

adding desulphonation buffer to the extraction chamber and controlled pumping the desulphonation buffer over the extraction membrane to perform alkali desulphonation of the converted DNA; and eluting the converted DNA from the extraction membrane.

In preferred embodiments of the present invention, the immediate heating of the nucleic acid source is to a temperature between 40° C. and 60° C., and/or the controlled pumping is preferably with a flow rate slower than or equal to 0.1 ml/s, between 0.001 ml/s and 0.1 ml/s, more preferably between 0.001 and 0.0017 ml/s.

Lysate: it is an aspect of the present invention to release nucleic acid(s) or DNA in a biological sample, enabling direct nucleic acid/DNA conversion and analysis in an automated system. According to the present invention, adding bisulfite to a nucleic acid or biological sample, for example a tissue sample, and heating the nucleic acid or sample containing DNA produces a lysate. Importantly, the lysate should be transportable through the automated system. The lysate comprises DNA which should be incubated with bisulfite and analyzed in the automated system (downstream nucleic acid/DNA analysis).

Lysis chamber or sample preparation chamber: here the sample is added into an automated system and lysis of the sample is performed, in the methods of the invention with bisulte under elevated temperature. The lysis chamber is the first step in the fluidic path through the cartridge. In a particular embodiment, the bottom of the lysis chamber is located directly above a heating element ("peltier") in the system. Preferably, the lysis chamber is designed to optimally transduce heat into the liquid above in the lysis chamber. In a preferred embodiment, all reaction temperatures within the lysis chamber are directly monitored by an infrared temperature measurement of the outer surface of the lysis chamber. Other means for measuring the reaction temperature of the lysis chamber may be used as well.

The source of a nucleic acid can be any source comprising a nucleic acid; it can be a biologic source of a nucleic acid, or any solution comprising a nucleic acid, for example DNA in a buffer solution.

The sample is a biological sample from a human or animal body, preferably a patient sample. The biological sample comprises nucleic acids or cells comprising DNA to be analysed according to the methods of the invention. The sample may be a tissue sample, swab specimen, body fluid, body fluid precipitate or lavage specimen. Non-limiting examples include human or animal fresh tissue samples, frozen tissue samples, tissue samples embedded in FFPE (formalin-fixed paraffin-embedded tissue), whole blood, blood plasma, blood serum, urine, stool, saliva, cerebrospinal fluid, peritoneal fluid, pleural fluid, lymph fluid, nipple aspirate, sputum and ejaculate. The samples may be collected using any suitable methods known in the art.

The present invention involves the use of an extraction membrane, e.g. for binding bisulfite-converted DNA and for the removal of bisulfite conversion reaction before downstream applications. The extraction membrane is present in the extraction chamber of a cartridge. Nucleic acids can be retained on the extraction membrane for further purification, concentration or processing. Suitable extraction membranes include glass and silica membranes. In preferred embodiments, the extraction membrane is a silica membrane. One or more silica membranes may be utilized as appropriate, such as 2, 3, 4 or 5 silica membranes, or a composite membrane comprising 2 or 3 silica membrane layers. In a particular embodiment, the extraction membrane according to the invention consists of 2 or 3 separate and distinct silica membranes stacked (closely) onto each other to form an extraction membrane, whereby the pumping of fluids in the extraction chamber is performed over/through said stacked silica membranes.

In an automated system the method is carried out in an automated process, which means that the method or steps of the process are carried out with an apparatus or machine capable of operating with little or no external control or influence by a human being. Suitable automated systems have been described in EP1896180, EP1904234 and EP2419705 and are accordingly incorporated in certain embodiments describing the present invention. Preferably, cartridge-based systems containing one or more reaction chambers and one or more fluid chambers are used. Some of the fluid chambers may hold fluid which is used for producing a lysate from the sample. Other chambers may hold fluids such as reaction buffers, washing fluids and amplification solutions. The reaction chambers are used to perform the different steps of the detection such as washing, lysis and amplification.

The term "cartridge" is to be understood as a self-contained assembly of chambers and/or channels, which is formed as a single object that can be transferred or moved as one fitting inside or outside of a larger instrument suitable for accepting (i.e. housing or connecting to) such cartridge. Some parts contained in the cartridge may be firmly connected whereas others may be flexibly connected and movable with respect to different cartridge components. As used herein, the term "cartridge" will mainly refer to a "fluidic cartridge" being a cartridge including at least one chamber or channel suitable for treating, processing, discharging, or analyzing a fluid, preferably a liquid.

The automated system can be an open or a closed, automated system. When a sample has been added or inserted in the cartridge-based system, the cartridge-based system is closed and stays closed during the operation of the system. The closed system contains all the necessary reagents on board, so the closed configuration provides the advantage that the system performs contamination-free detection. Alternatively, an open, accessible cartridge can be used in an automated system. The necessary reagents are added in the open cartridge as required, thereafter a sample can be inserted in the open cartridge and the cartridge can be run in a closed, automated system.

In a particular setting, the automated system consists of the following elements: an instrument, a console and cartridges. The instrument and console work in combination with the consumable cartridges. The instrument comprises control modules for performing assays. The console is a computer to control and monitor the instrument's actions and the cartridge status during the assays. In the cartridge the assay will be run. After inserting a sample in a cartridge, pre-loaded with reagents, the cartridge is loaded into the instrument and the instrument controls the assay which is performed autonomously in the cartridge. After the assay has run, the console software processes the results and generates a report accessible for the end-user of the automated system.

In preferred embodiments describing the present invention, all reagents required for performing a methylated DNA detection assay are pre-positioned within the cartridge so that the cartridge is a self-contained disposable apparatus for performing nucleic acid assays. Suitable means include biochips based on a DNA microarray or protein microarray, and/or devices for conducting thermocycling (e.g. PCR, LCR, and others) and/or means for sequencing. Preferably, the cartridge will incorporate means for performing thermocycling, preferably polymerase chain reaction (PCR) or reverse transcription polymerase chain reaction (RT-PCR). PCR methods are well known in the art and rely on thermal cycling, consisting of cycles of repeated heating and cooling of the reaction for nucleic acid melting and enzymatic replication of the nucleic acid. Such amplification reactions typically employ target nucleic acid and reaction components such as a heat-stable DNA polymerase (for instance Taq polymerase), nucleotides and oligonucleotides (for instance primers, probes, blockers . . . ) required for initiation of nucleic acid synthesis. In preferred applications, the automated system will apply thermocycling using reagents in dried-down form present in the system. The sample will be treated as described in the present invention to form a lysate comprising nucleic acid, and reagents pre-positioned in the automated system are reconstituted at the point of running an assay on the sample/testing the sample in the automated system. The nucleic acid will be eluted (from an extraction membrane) in the automated system. Accordingly, the eluate allows for downstream PCR/nucleic acid analysis directly in the automated system. Typically, micro pneumatic controllers are used to direct ("pumping") the lysate, the reagents and the eluate as required for completing the assay. Assays may include end-point or real time detection; both methods are well known in the art.

Pumping: in a particular embodiment of the invention "pumping" means the transport or moving of fluids (liquids or gases) through the extraction chamber/through the extraction membrane. "controlled pumping" Means controlled pumping in an automated system or means that the flow rate can be specified in a system. The automated system thus controls the flow rate of the pumping of fluids in the automated system (which is different compared to using for example gravity or centrifugal force(s) to move fluids from one place to another). Controlled pumping (flow control) allows for optimal binding of a nucleic acid to an extraction membrane and removing reagents or buffers from a source containing nucleic acid.

Applications include optimal removal of bisulfite reagent by controlled pumping of a binding buffer-and-lysate-solution over an extraction membrane, and optimal desulphonation of a base deaminated in a nucleic acid and conversion of said base to an uracil base by adding desulphonation buffer and controlled pumping of the desulphonation buffer over an extraction membrane. Controlled pumping has the advantage that a system can apply variable speed pumping as required in said system. This is especially useful in controlling the method steps of the invention as described herein.

Flow rate: in a particular embodiment of the invention the "flow rate" means the pumping speed of fluids passing through the extraction chamber/through the extraction membrane. In a preferred embodiment, the flow rate is expressed in ml/s.

Currently available kits for methylated DNA detection require the preparation of the sample, such as DNA purification (for example DNA purification from blood, tissue or cells) and a DNA denaturation step (typically by heating the sample containing DNA at 98° C. for 10 minutes). These preparative steps have been eliminated in the methods of the present invention. Thus, contrary to existing nucleic acid conversion methods and systems, which involve a nucleic acid purification and subsequent nucleic denaturation step, 10 min heating at 95° C. to 98° C. prior to treatment with nucleic acid conversion reagent, the present invention keeps the sample at a reaction temperature below 98° C., preferably below 95° C., below 94° C., below 93° C., below 92° C., below 91° C., below 90° C., below 85° C., below 80° C., below 70° C., below 60° C. without largely affecting sensitive and specific downstream methylation detection. Indeed, the nucleic acid conversion reagent is added directly to the nucleic acid or sample and directly heated to a reaction temperature between 40° C. and 60° C., between 45° C. and 55° C., more preferably between 49° C. and 53° C. to produce a lysate. More preferably, the reaction temperature for producing the lysate is 40° C., 42° C., 44° C., 46° C., 48° C., 49° C., 50° C., 50.5° C., 51° C., 51.5° C., 52° C., 53° C., 54° C., 56° C., 58° C., 59° C., 60° C., 62° C., 64° C., 66° C., 68° C., 70° C., 72° C., 74° C., 76° C., 78° C., 80° C. In a particular embodiment, the reaction temperature for producing the lysate is 51° C.

The nucleic acid/sample is heated in the lysis chamber. The automated system, more particularly the instrument, contains a heating element which is able to warm the lysis chamber through the wall of the lysis chamber to a given reaction temperature. The time required to reach a reaction temperature in the lysis chamber is related to/proportional to the requested temperature and to the volume of the fluids inside the lysis chamber (the lysate) to be heated. According to the height of the reaction temperature required and the volume to be heated, it may take up to 5 minutes, 10 minutes, 15 minutes, 20 minutes, 25 minutes or 30 minutes to reach the requested temperature. The automated system controls the reaction temperature inside the lysis chamber by a temperature measurement of the outer surface of the lysis chamber. However, it can be up to 25° C. warmer inside the lysis chamber than the temperature of the outer surface of the lysis chamber. It is estimated that when the wall temperature of the lysis chamber is set to 40° C. and with 700 μl of the conversion reagent present inside the lysis chamber, that the reaction temperature within the lysis chamber is 51° C.

Similarly, the extraction chamber, with therein an extraction membrane, can be heated by a heating element located inside the automated system, more particularly inside the instrument, and located in close proximity to the extraction chamber. The heating element is able to warm the extraction chamber through the wall of the extraction chamber. In one embodiment of the invention, a wash step is performed after the bisulfite removal step by adding wash buffer to the extraction chamber and pumping the wash buffer over the extraction membrane with a temperature of 40° C. with a flow rate slower than or equal to 0.1 ml/s. In another embodiment of the invention, desulphonation is performed by adding desulphonation buffer to the extraction chamber and pumping the desulphonation buffer over the extraction membrane with a temperature of 20° C. with a flow rate as described herein.

All methods, cartridges and systems of the present invention directly add bisulfite solution to the nucleic acid/sample and control nucleic acid degradation by employing a lower heat temperature and a longer incubation time to produce a lysate comprising nucleic acid/DNA. In preferred embodiments, the heating is 30 minutes to 1 hour at a suitable reaction temperature, preferably at a reaction temperature of 40 to 60° C. To attain optimal sensitivity and specificity, the heating time is around 1 hour at a temperature of 40 to 60° C., the heating time is preferably 30 min, 35 min, 40 min, 45 min, 50 min, 51 min, 52 min, 53 min, 54 min, 55 min, 56 min, 57 min, 58 min, 59 min, 60 min, 61 min, 62 min, 63 min, 64 min, 65 min, 66 min, 67 min, 68 min, 69 min, 70 min, 75 minutes, 80 minutes at the temperature as suitable. Measurement of the temperature is detailed elsewhere in present description.

The invention requires solutions to be pumped over the extraction membrane and typically the pumping steps involve controlled pumping in an automated system, more preferably slow pumping, e.g pumping with a flow rate slower than or equal to 0.1 ml/s, preferably with a flow rate between 0.001 ml/s and 0.1 ml/s, more preferably with a flow rate between 0.001 and 0.0017 ml/s. In a particular embodiment, in the methods according to the invention there is at least one flow rate between 0.001 and 0.0017 ml/s.

Several of the currently available kits for methylated DNA detection perform bisulfite removal using a low-elution spin column that is first washed with binding buffer, whereafter the converted DNA solution is added to the column in order to remove the bisulfite conversion reagent. According to the present invention, after bisulfite conversion binding buffer is added to the lysate and the binding buffer-and-lysate-solution is pumped over an extraction membrane with a flow rate slower than or equal to 0.1 ml/s, preferably with a flow rate between 0.001 ml/s and 0.1 ml/s, more preferably between 0.001 and 0.0017 ml/s to remove the bisulfite conversion reagent, without the need for an elution column step.

Several of the currently available kits for methylated DNA detection require multiple centrifuge steps. In these kits the desulphonation step is performed by incubating the converted DNA solution with desulphonation buffer for 20 minutes at room temperature, followed by a centrifuge step; then wash buffer is added, followed by a next centrifuge step; then an elution buffer is added, again followed by a centrifuge step to elute the converted DNA. According to the present invention, the desulphonation step is performed by adding desulphonation buffer to the converted DNA solution in the automated system and pumping the desulphonation buffer over the extraction membrane with a flow rate slower than or equal to 0.1 ml/s, preferably with a flow rate between 0.001 ml/s and 0.1 ml/s, more preferably between 0.001 and 0.0017 ml/s, without a centrifuge step. Similarly, the wash steps and elution of the converted DNA from the extraction membrane is performed by pumping elution buffer over the extraction membrane with a flow rate slower than or equal to 0.1 ml/s, without the requirement for any centrifuge steps.

Optimal binding of the nucleic acid from the binding buffer-and-lysate solution to the extraction membrane will involve a flow rate slower than or equal to 0.1 ml/s, or between 0.001 ml/s and 0.1 ml/s, or between 0.001 and 0.0017 ml/s, preferable a flow rate not higher than 0.1 ml/s, 0.090 ml/s, 0.080 ml/s, 0.075 ml/s, 0.070 ml/s, 0.0625 ml/s, 0.060 ml/s, 0.050 ml/s, 0.040 ml/s, 0.030 ml/s, 0.020 ml/s, 0.01 ml/s, 0.0090 ml/s, 0.0080 ml/s, 0.0070 ml/s, 0.0060 ml/s, 0.0050 ml/s, 0.0040 ml/s, 0.0030 ml/s, 0.0020 ml/s, 0.0019 ml/s, 0.0018 ml/s, 0.0017 ml/s, 0.0016 ml/s, 0.0015 ml/s, 0.0014 ml/s, 0.0013 ml/s, 0.0012 ml/s, 0.0011 ml/s or 0.0010 ml/s. Most preferably optimal binding of the nucleic acid from the binding buffer-and-lysate solution to the extraction membrane will involve a flow rate of 0.1 ml/s.

Bisulfite removal from the binding buffer-and-lysate solution by pumping the binding buffer-and-lysate solution over the extraction membrane will involve a flow rate slower than or equal to 0.1 ml/s, or between 0.001 ml/s and 0.1 ml/s, or between 0.001 and 0.0017 ml/s, preferable a flow rate not higher than 0.1 ml/s, 0.090 ml/s, 0.080 ml/s, 0.075 ml/s, 0.070 ml/s, 0.0625 ml/s, 0.060 ml/s, 0.050 ml/s, 0.040 ml/s, 0.030 ml/s, 0.020 ml/s, 0.01 ml/s, 0.0090 ml/s, 0.0080 ml/s, 0.0075 ml/s, 0.0070 ml/s, 0.0060 ml/s, 0.0050 ml/s, 0.0040 ml/s, 0.0030 ml/s, 0.0020 ml/s, 0.0019 ml/s, 0.0018 ml/s, 0.0017 ml/s, 0.0016 ml/s, 0.0015 ml/s, 0.0014 ml/s, 0.0013 ml/s, 0.0012 ml/s, 0.0011 ml/s or 0.0010 ml/s. Most preferably, optimal bisulfite removal from the binding buffer-and-lysate solution over the extraction membrane will involve a flow rate of 0.1 ml/s.

Optimal desulphonation of the nucleic acid by pumping desulphonation buffer over the extraction membrane will involve a flow rate slower than or equal to 0.1 ml/s, or between 0.001 ml/s and 0.1 ml/s, or between 0.001 and 0.0017 ml/s, preferable a flow rate not higher than 0.1 ml/s, 0.090 ml/s, 0.080 ml/s, 0.075 ml/s, 0.070 ml/s, 0.0625 ml/s, 0.060 ml/s, 0.050 ml/s, 0.040 ml/s, 0.030 ml/s, 0.020 ml/s, 0.01 ml/s, 0.0090 ml/s, 0.0080 ml/s, 0.0075 ml/s, 0.0070 ml/s, 0.0060 ml/s, 0.0050 ml/s, 0.0040 ml/s, 0.0030 ml/s, 0.0020 ml/s, 0.0019 ml/s, 0.0018 ml/s, 0.0017 ml/s, 0.0016 ml/s, 0.0015 ml/s, 0.0014 ml/s, 0.0013 ml/s, 0.0012 ml/s, 0.0011 ml/s or 0.0010 ml/s. Most preferably optimal desulphonation of the nucleic acid by pumping desulphonation buffer over the extraction membrane will involve a flow rate of 0.0017 ml/s.

The (alkali) desulphonation is performed by pumping the desulphonation buffer over an extraction membrane with a flow rate slower than or equal to 0.1 ml/s. For the alkali desulphonation of the converted DNA-pumping step the flow rate should preferably be kept very slow, preferably not higher than 0.01 ml/s, 0.075 ml/s, 0.0625 ml/s, 0.0090 ml/s, 0.0080 ml/s, 0.0075 ml/s, 0.0070 ml/s, 0.0060 ml/s, 0.0050 ml/s, 0.0040 ml/s, 0.0030 ml/s, 0.0020 ml/s, more preferably not higher than 0.0017 ml/s, even more preferably between 0.001 and 0.0017 ml/s. By keeping the flow rate of the pumping over the extraction membrane low, impurities and unwanted elements in the sample, which may be formed during the bisulfite conversion for example, are removed properly from the treated sample when pumped over the membrane. The bisulfite removal from the lysate-pumping step may be performed somewhat faster than the (alkali) desulphonation of the converted DNA-pumping step.

In one preferred embodiment of the invention, a method is provided for a detection of a nucleic acid methylation status in an automated system comprising an extraction chamber comprising an extraction membrane, said method comprising the steps of, or characterized by:
  introducing a source of the nucleic acid into the automated system, adding bisulfite to the nucleic acid and immediately followed by heating the source of the nucleic acid to a temperature between 40° C. and 60° C. to produce a lysate comprising the nucleic acid and to deaminate an unmethylated cytosine base present in said nucleic acid present in said lysate;
  adding binding buffer to the lysate to produce a binding buffer-and-lysate-solution;
  binding the nucleic acid to the extraction membrane and removing the bisulfite by pumping the binding buffer-and-lysate-solution over the extraction with a flow rate between 0.001 ml/s and 0.0017 ml/s,
  adding desulphonation buffer to the extraction chamber and pumping the desulphonation buffer over the extraction membrane with a flow rate between 0.001 ml/s and 0.0017 ml/s, to desulphonate the base deaminated in the first step in the nucleic acid and to convert said base to an uracil base;
  eluting the converted nucleic acid from the extraction membrane; and
analyzing the converted nucleic acid in the automated system.

In a further preferred embodiment, a method is provided for a detection of methylated DNA via bisulfite conversion of DNA in a sample in an automated system comprising an extraction chamber comprising an extraction membrane, said method comprising the steps of, or characterized by:
  introducing a sample into the automated system, adding bisulfite to the sample and immediately heating the sample to a temperature between 40° C. and 60° C. to produce a lysate comprising DNA and to perform bisulfite conversion of said DNA;
  adding binding buffer to the lysate comprising DNA to produce a binding buffer-and-lysate-solution;
  binding the DNA to the extraction membrane and removing the bisulfite by pumping the binding buffer-and-lysate-solution over the extraction membrane with a flow rate between 0.001 ml/s and 0.0017 ml/s;
  adding desulphonation buffer to the extraction chamber and pumping the desulphonation buffer over the extraction membrane with a flow rate between 0.001 ml/s and 0.0017 ml/s to perform alkali desulphonation of the converted DNA;
  eluting the converted DNA from the extraction membrane; and
analyzing the converted DNA in the automated system.

According to the invention, the bisulfite removal step and (alkali) desulphonation step is performed by pumping respectively the binding buffer-and-lysate-solution and the desulphonation buffer over an extraction membrane sequentially in two separate and distinct pumping steps over said (one and the same) extraction membrane. In a yet more preferred embodiment, the bisulfite removal step and (alkali) desulphonation step is performed by pumping over an extraction membrane sequentially, whereby the desulphonation-pumping step is performed slower than the bisulfite removal-pumping step. Additionally, wash buffer may be pumped over the extraction membrane in one or more washing steps, which are preferably between the bisulfite removal-pumping step and the (alkali) desulphonation-pumping step, and again after the (alkali) desulphonation-pumping step. In a preferred embodiment, wash buffer is pumped over the extraction membrane with a flow rate of 0.0625 ml/s.

In one embodiment of the invention, a method is provided for a detection of a nucleic acid methylation status in an automated system comprising an extraction chamber comprising an extraction membrane, said method comprising the steps of, or characterized by:
  introducing a source of the nucleic acid into the automated system, adding bisulfite to the nucleic acid and immediately followed by heating the source of the nucleic acid to a temperature between 40° C. and 60° C. to produce a lysate comprising the nucleic acid and to deaminate an unmethylated cytosine base present in said nucleic acid;
  adding binding buffer to the lysate to produce a binding buffer-and-lysate-solution;
  binding the nucleic acid to the extraction membrane and removing the bisulfite by pumping the binding buffer-and-lysate-solution over the extraction membrane with a flow rate slower than or equal to 0.1 ml/s and in a time period between 2 and 15 minutes;
  adding desulphonation buffer to the extraction chamber and pumping the desulphonation buffer over the extraction membrane with a flow rate slower than or equal to 0.1 ml/s and in a time period between 6 and 20 minutes, to desulphonate the base deaminated in the first step in the nucleic acid and to convert said base to an uracil base;

eluting the converted nucleic acid from the extraction membrane; and analyzing the converted nucleic acid in the automated system.

In a similar way as already described herein, a method is provided for a detection of methylated DNA via bisulfite conversion of DNA in a sample in an automated system comprising an extraction chamber comprising an extraction membrane, said method comprising the steps of:

introducing a sample into the automated system, adding bisulfite to the sample and immediately followed by heating the sample to a temperature between 40° C. and 60° C. to produce a lysate comprising the DNA and to perform bisulfite conversion of the DNA, adding binding buffer to the lysate comprising DNA to produce a binding buffer-and-lysate-solution;

binding the DNA to the extraction membrane and removing the bisulfite by pumping the binding buffer-and-lysate-solution over the extraction membrane with a flow rate slower than or equal to 0.1 ml/s and in a time period between 2 and 15 minutes;

adding desulphonation buffer to the extraction chamber and pumping the desulphonation buffer over the extraction membrane with a flow rate slower than or equal to 0.1 ml/s and in a time period between 6 and 20 minutes to perform alkali desulphonation of the converted DNA;

eluting the converted DNA from the extraction membrane; and analyzing the converted DNA in the automated system.

As described, the efficacy of the bisulfite conversion process is improved and allows for minimal DNA degradation. The methods of the invention are therefore particularly useful for the methylation analysis of samples with relatively small amounts of genomic DNA. For example, some samples can include 10, 9, 8, 7, 6, 5, 4, 3, 2, or 1 nanograms of DNA. Other samples can include as little as 500, 400, 300, 200, or 100 picograms of DNA. Such samples are exemplified, by urine and plasma, which include relatively small amounts of circulating DNA. In this regard, the methods of the invention are useful for the analysis of samples that include otherwise depleted or scarce genomic DNA.

The methods of the invention find their application in automated systems. In certain embodiments, the automated systems will hold a cartridge for the detection of methylated DNA in a sample. In an embodiment of the present invention a cartridge is used for the detection of methylated DNA in a sample according to the methods of the invention, for example in a human tissue sample. Preferably, the cartridge comprises an extraction chamber, which extraction chamber contains an extraction membrane. Even more preferably, the cartridge comprises a lysis chamber and an extraction chamber, which extraction chamber contains an extraction membrane, and wherein there is a channel between the lysis chamber and the extraction chamber for transporting fluids from the lysis chamber to the extraction chamber. The channel is a fluidic path within the cartridge connecting the lysis chamber to the extraction chamber. The channel can be a simple channel or a channel containing itself further chambers between the lysis chamber and the extraction chamber. Even more preferably, the cartridge comprises a lysis chamber, an extraction chamber, which extraction chamber contains an extraction membrane, and wherein there is a channel between the lysis chamber and the extraction chamber for transporting fluids from the lysis chamber to the extraction chamber, and a PCR module for the PCR process steps in the cartridge.

Thus, suitable cartridges comprise a plurality of chambers, preferably at least three chambers: a lysis chamber, an extraction chamber, which extraction chamber contains an extraction membrane, and a PCR chamber allowing for downstream DNA analysis. Other chambers may be required for the storage of reagents suitable of use in the process for methylation detection of the nucleic acid. Fluidic channels provide connection between the different chambers and allow for the transport of fluids (liquids and gases) from one chamber to another as required by the methods as described in the present invention.

Typically, the lysis chamber in the cartridge is susceptible of:

receiving a sample, adding bisulfite solution to the sample, heating the sample directly to 40° C. and 60° C. to produce a lysate comprising DNA and to perform bisulfite conversion of the DNA in the lysate, adding binding buffer to the lysate.

The bisulfite solution and the binding buffer will be stored in further chambers or containers in the cartridge and the further chambers or containers are in connection with the lysis chamber through a fluidic channel.

As detailed elsewhere in the description, the extraction chamber in the cartridge contains an extraction membrane. The extraction chamber in the cartridge is susceptible of:

receiving the lysate, allowing subsequent removal of the bisulfite by pumping the binding buffer-and-lysate-solution over the extraction membrane with a flow rate slower than or equal to 0.1 ml/s, between 0.001 ml/s and 0.1 ml/s, more preferably between 0.001 and 0.0017 ml/s, allowing subsequent addition of desulphonation buffer to the extraction chamber and pumping the desulphonation buffer over the extraction membrane with a flow rate slower than or equal to 0.1 ml/s, between 0.001 ml/s and 0.1 ml/s, more preferably between 0.001 and 0.0017 ml/s, to perform alkali desulphonation of the converted DNA, and allowing subsequent elution of the converted DNA from the extraction membrane.

In order to allow performance of the different steps, there is a channel between the lysis chamber and the extraction chamber for transporting fluids from the lysis chamber to the extraction chamber. The cartridge also contains a PCR chamber allowing for downstream analysis of the converted DNA. Between the extraction chamber and the PCR chamber exists a fluid channel for transporting converted DNA from the extraction chamber to the PCR chamber.

The invention provides a cartridge for detection of a nucleic acid methylation status according to the methods of the invention in an automated system, said cartridge comprising an extraction chamber comprising an extraction membrane, bisulfite, binding buffer and desulphonation buffer. The extraction membrane in the extraction chamber of the cartridge is susceptible of binding the nucleic acid and removing the bisulfite when the binding buffer-and-lysate solution is transported over the extraction membrane.

The invention also provides a cartridge for detection of a nucleic acid methylation status, the cartridge comprising:

a lysis chamber susceptible of receiving a source of the nucleic acid, adding bisulfite solution to the source of the nucleic acid, and immediately followed by heating the source of the nucleic acid to a temperature between 40° C. and 60° C. to produce a lysate comprising the nucleic acid and to deaminate an unmethylated cytosine base present in said nucleic acid, and adding binding buffer to the lysate to form a binding buffer-and-lysate-solution;

an extraction chamber comprising an extraction membrane susceptible of receiving the binding buffer-and-lysate-solution, allowing subsequent removal of the bisulfite by pumping the binding buffer-and-lysate-solution over the extraction membrane with a flow rate slower than or equal to 0.1 ml/s, between 0.001 ml/s and 0.1 ml/s, more preferably between 0.001 and 0.0017 ml/s, allowing subsequent addition of desulphonation buffer to the extraction chamber and pumping the desulphonation buffer over the extraction membrane with a flow rate slower than or equal to 0.1 ml/s, between 0.001 ml/s and 0.1 ml/s, more preferably between 0.001 and 0.0017 ml/s, to desulphonate the base deaminated in the first step in the nucleic acid and to convert said base to an uracil base, and allowing subsequent elution of the converted nucleic acid from the extraction membrane, wherein there is a channel between the lysis chamber and the extraction chamber for transporting fluids from the lysis chamber to the extraction chamber, and, a PCR chamber allowing downstream analysis of the converted nucleic acid, wherein there is a channel between the extraction chamber and the PCR chamber for transporting the converted nucleic acid from the extraction chamber to the PCR chamber.

The invention also provides a cartridge for detection of methylated DNA in a sample, the cartridge comprising:

a lysis chamber susceptible of receiving a sample, adding bisulfite solution to the sample, heating the sample to produce a lysate comprising DNA and to perform bisulfite conversion of the DNA in the lysate, and adding binding buffer to the converted lysate to form a binding buffer-and-lysate-solution, an extraction chamber with therein an extraction membrane susceptible of receiving the binding buffer-and-lysate-solution, allowing subsequent removal of the bisulfite by pumping the binding buffer-and-lysate-solution over the extraction membrane with a flow rate slower than or equal to 0.1 ml/s, between 0.001 ml/s and 0.1 ml/s, more preferably between 0.001 and 0.0017 ml/s, allowing subsequent addition of desulphonation buffer to the extraction chamber and pumping the desulphonation buffer over the extraction membrane with a flow rate slower than or equal to 0.1 ml/s, between 0.001 ml/s and 0.1 ml/s, more preferably between 0.001 and 0.0017 ml/s, to perform alkali desulphonation of the converted DNA, and allowing subsequent elution of the converted DNA from the extraction membrane, wherein there is a channel between the lysis chamber and the extraction chamber for transporting fluids from the lysis chamber to the extraction chamber, and, a PCR chamber allowing downstream analysis of the converted DNA, wherein there is a channel between the extraction chamber and the PCR chamber for transporting converted DNA from the extraction chamber to the PCR chamber.

In a most preferred embodiment, the cartridge contains a lysis chamber, 8 reagent containers, a filter area, an extraction chamber, with therein an extraction membrane, a PCR chamber and a waste chamber and all the connecting channels. The reagent containers store the necessary reagents needed for the detection of methylated nucleic acid or DNA (desulphonation buffer, wash buffers etc.).

The invention also provides for a system for automatic detection of methylated DNA, which system is suitable for executing the methods of the present invention. Application of the methods as described may require the automatic system to receive a cartridge as described.

In a particular embodiment of the invention, in the automated system a cartridge is inserted/loaded, which cartridge comprises a lysis chamber and an extraction chamber, with therein an extraction membrane, and wherein there is a fluidic channel between the lysis chamber and the extraction chamber, wherein the fluidic channel contains a filter. The instrument, which is one of the elements of the automated system, controls the assay steps (the bisulfite conversion of DNA in a sample) to be performed inside the cartridge. The cartridge is pre-loaded with the necessary reagents and buffers. After introducing the sample in the lysis chamber of the cartridge, the cartridge is loaded into the instrument and the instrument controls the assay which is performed autonomously in the cartridge. Bisulfite is added to the sample in the lysis chamber of the cartridge and the reaction temperature in the lysis chamber is elevated to at least 40 to 60° C. to perform bisulfite conversion of the DNA in the sample. After the bisulfite conversion in the lysis chamber, binding buffer is added into the lysis chamber to produce a binding buffer-and-lysate-solution. From the lysis chamber, the binding buffer-and-lysate-solution is led through a channel towards the extraction chamber in the cartridge. The channel can be foreseen of one or more filters. The main function of those filters is clean-up the lysate, to remove debris formed in the lysis chamber, to remove any particles that may be large enough to block any of the downstream narrow channels in the automated system or cartridge. In the extraction chamber the DNA from the lysate is binded to the extraction membrane and the bisulfite is removed by pumping the binding buffer-and-lysate-solution over the extraction membrane with a flow rate as described. Then wash buffer, comprising ethanol, is pumped over the extraction membrane with a flow rate between 0.001 ml/s and 0.1 ml/s to remove any possible remaining binding buffer-and-lysate-solution. Desulphonation buffer is added into the extraction chamber and pumped over the extraction membrane with a flow rate as described to perform alkali desulphonation of the converted DNA. From this particular embodiment, it is understood to the person skilled in the art that the automated system or cartridge of the invention may also comprise a filter. In a particular embodiment, the cartridge thus comprises a filter in the channel between the lysis chamber and the extraction chamber, and an extraction membrane in the extraction chamber. It is clear that such a filter performs a filter function when fluids passes through said filter. The filter may have a single filter configuration or a three-stack filter configuration for more difficult samples.

Thus, in another aspect, the present invention is directed to an automated system for a detection of a nucleic acid methylation status in a source of a nucleic acid, the automated system adapted for receiving a cartridge comprising an extraction chamber comprising an extraction membrane, said system controlling the steps of:

adding bisulfite to a source of a nucleic acid introduced into the automated system and immediately followed by heating the source of the nucleic acid to a temperature between 40° C. and 60° C. to produce a lysate comprising the nucleic acid and to deaminate an unmethylated cytosine base present in said nucleic acid, adding binding buffer to the lysate comprising nucleic acid to produce a binding buffer-and-lysate-solution, binding the nucleic acid to the extraction membrane and removing the bisulfite by pumping the binding buffer-and-lysate-solution over the extraction membrane with a flow rate slower than or equal to 0.1 ml/s, or between 0.001 ml/s and 0.1 ml/s, more preferably between 0.001 and 0.0017 ml/s, adding desulphonation buffer to the extraction chamber and pumping the desulphonation buffer over the extraction membrane with a flow rate slower than or equal to 0.1 ml/s, between 0.001 ml/s and 0.1 ml/s, more preferably between 0.001 and 0.0017 ml/s, to desulphonate the base deaminated in the first step in the nucleic acid and to convert said base to an uracil base, eluting the converted nucleic acid from the extraction membrane, and analyzing the converted nucleic acid.

The present invention also envisages a system for automatic detection of methylated DNA via bisulfite conversion of DNA in a sample, the system adapted for receiving a cartridge with at least an extraction chamber, with therein an extraction membrane, the system controlling the steps of:

adding bisulfite to a sample introduced in the automated system and heating the sample directly between 40° C. and 60° C. to produce a lysate comprising DNA and to perform bisulfite conversion of the DNA;

adding binding buffer to the lysate comprising DNA to produce a binding buffer-and-lysate-solution;

binding the DNA to the extraction membrane and removing the bisulfite by pumping the binding buffer-and-lysate-solution over the extraction membrane with a flow rate slower than or equal to 0.1 ml/s, or between 0.001 ml/s and 0.1 ml/s, more preferably between 0.001 and 0.0017 ml/s;

adding desulphonation buffer to the extraction chamber and pumping the desulphonation buffer over the extraction membrane with a flow rate slower than or equal to 0.1 ml/s, between 0.001 ml/s and 0.1 ml/s, more preferably between 0.001 and 0.0017 ml/s, to perform alkali desulphonation of the converted DNA;

eluting the converted DNA from the extraction membrane; and analyzing the converted DNA.

The automated system contains elements to pump fluids from one place to another. The pumping systems of the system can be adjusted to pump liquids over an extraction membrane within the cartridge with a specific growth rate as required. The pumping steps over an extraction membrane are mechanically performed as programmed in the automated system and replace the manual clean-up of the sample (e.g. bisulfite removal, desulphonation and washing steps) by processing the sample over low-elution spin columns and/or by centrifuge. Such automation allows for a high-throughput of samples in a short time, without any human interaction during the method steps of the invention.

In an embodiment of the invention, the pumping steps over an extraction membrane can be performed in 2 or more pumping steps over the extraction membrane, for example by pumping a volume of desulphonation buffer in 2 times half of the original volume of the desulphonation buffer over an extraction membrane. Similarly, the pumping during the wash steps, e.g. the pumping of the sample with the wash buffer over an extraction membrane, can be performed in more than 1 pumping step. In one embodiment, the first washing step is performed in 1 pump step and the last wash step is performed in 3 pump steps. In another example the first washing step is performed in 3 pumps and the last wash step is performed in 7 pumps.

In a preferred embodiment, the sample used in the methods, cartridges and systems of the invention is a human tissue sample.

In a preferred embodiment of the invention, the DNA analysis/nucleic acid analysis in the automated system comprises DNA amplification/nucleic acid amplification. Particularly preferred amplification methods according to the invention are methylation specific PCR methods (MSP) which are known in the art, for example a real time-PCR (RT-PCR) reaction using a bisulfite converted specific assay.

In a preferred embodiment, the method may further comprise the step of detecting the amplified nucleic acid. There are probe-based assays which exploit the oligonucleotide hybridization to specific sequences and subsequent detection of the hybrid. It is also possible to sequence the target nucleic acid after further steps known by the person skilled in the art. In a particularly preferred embodiment of the invention, the nucleic acid is detected by measuring the intensity of fluorescence light during amplification, for example with a specific signal for detecting the un-methylated converted DNA and a specific signal for detecting the methylated DNA. This method entails the monitoring of real time fluorescence.

Typically, the methylation status of a panel of genes comprising at least one of the genes together with one, two, three, four or five additional genes is assessed, wherein a change in methylation status in at least one of the genes in the panel is indicative of a predisposition to, or the incidence of a disease, such as cancer. The term "methylation status" refers to the presence or absence of a methylated cytosine residue in one or more CpG dinucleotides within the nucleic acid or gene of interest. In many genes, the CpG islands are found in the promoter region and may begin (just) upstream of a promoter and extend downstream into the transcribed region. When the CpG distribution in the promoter region is rather scarce, levels of methylation may be assessed in the intron and/or exon regions. The region for assessment may be a region that comprises both intron and exon sequences and thus overlaps both regions.

Preferably the methods according to the invention are used in diagnostics, for the screening of tissue or fluids from the human or even animal body for the presence of certain methylation patterns. The presence or absence of methylated cytosine bases in the nucleic acid or DNA is indicative of a cell proliferative disorder. The methods according to the invention are used to enhance the speed and user friendliness (no manual handlings) of the detection of methylation sites in nucleic acids.

Alternatively, the methods according to the invention are used for detecting a predisposition to, or the incidence of, cancer in a sample, wherein the detection of a change in the methylated DNA status is indicative of a predisposition to, or the incidence of, cancer. The method as described may be used in predicting the likelihood of resistance to treatment of cancer with a cancer inhibitor or, of selecting a suitable treatment regimen for cancer. Or, the methods may be used for predicting the likelihood of resistance to/successful treatment of cancer with a cancer inhibitor, wherein detection of the methylation change is indicative that the likelihood of resistance to treatment is lower/higher than if the methylation modification is not detected. A further use may involve selecting a suitable treatment regimen for cancer wherein detection of the methylation status change results in selection of a cancer inhibitor and wherein if the methylation change is not detected the cancer inhibitor is not selected for treatment, or the opposite way.

Further to the already extensively described automated systems of the present invention, in a most preferred embodiment, the automated system applies a method for a detection of methylated DNA in a patient sample in an automated system containing a cartridge including a lysis chamber, an extraction chamber, with therein an extraction membrane, comprising the steps of:

- introducing a patient sample in the lysis chamber of the automated system,
- adding bisulfite to the sample in the lysis chamber and immediately followed by heating for 1 hour at a temperature between 40° C. and 60° C. inside the lysis chamber to produce a lysate comprising DNA and to perform bisulfite conversion of the DNA,
- adding binding buffer to the lysate comprising DNA to produce a binding buffer-and-lysate-solution,
- transporting the binding buffer-and-lysate-solution from the lysis chamber to the extraction chamber, which extraction chamber contains an extraction membrane,
- binding the DNA from the lysate to the extraction membrane and removing the bisulfite by pumping the binding buffer-and-lysate-solution over the extraction membrane with a flow rate between 0.001 ml/s and 0.1 ml/s, more preferably between 0.001 and 0.0017 ml/s, to remove the bisulfite, the binding buffer and the lysate whilst the DNA from the lysate is being withheld onto the extraction membrane,
- pumping wash buffer, comprising ethanol, over the extraction membrane with a flow rate between 0.001 ml/s and 0.1 ml/s to remove any possible remaining binding buffer-and-lysate-solution,
- adding desulphonation buffer to the extraction chamber and pumping the desulphonation buffer over the extraction membrane with a flow rate between 0.001 ml/s and 0.1 ml/s, more preferably between 0.001 and 0.0017 ml/s to perform alkali desulphonation of the converted DNA,
- adding wash buffer, comprising ethanol, to the extraction chamber and pumping the wash buffer over the extraction membrane in at least 3 pump steps, more preferably 7 pump steps, with a flow rate between 0.001 ml/s and 0.1 ml/s to remove any possible remaining desulphonation buffer,
- performing ethanol evaporation by pumping air with a flowrate of 0.1 ml/s over the extraction membrane,
- eluting the converted DNA from the extraction membrane by pumping an elution buffer or water with a flow rate between 0.001 ml/s and 0.1 ml/s over the extraction membrane, and analyzing the converted DNA in the automated system.

The temperature of the lysis chamber in a cartridge in the automated system can be regulated by adjusting the wall temperature of the lysis chamber to a specific temperature of choice. In a particular embodiment, the wall temperature of the lysis chamber was raised to at least 40° C. by heating the peltier of the automated system to 40° C. The peltier is an element used for heating (the liquids within) the lysis chamber, which is located at the outer surface of the lysis chamber. Setting of the wall temperature on 40° C. means that the real reaction temperature inside the lysis chamber of the cartridge is at least 40° C., or even around 50° C. to 60° C. inside the lysis chamber. So in the methods of the invention, the temperature directly goes from room temperature to a reaction temperature of at least or equal to 40° C.: when the conversion reagent (bisulfite) is added to the patient sample in the lysis chamber, the reaction temperature is immediately raised to at least 40° C. or even to around 50 to 60° C. in the lysis chamber for 1 hour to produce a lysate and to deaminate the cytosine base in the nucleic acid in said patient sample (to perform bisulfite conversion of the DNA in said patient sample). In the Zymo Research EZ DNA Methylation-Lightning™ Kit protocol, it is stated that the bisulfite conversion reagent is added to the DNA sample and then the temperature is elevated to 98° C. for 8 minutes, and in a next step to 54° C. for 60 minutes. So in the automated system this first step, namely the heating at 98° C., has been eliminated. Alternatively, the conversion reagent (bisulfite) is already present in the lysis chamber upon sample insertion. So when the patient sample is added in the lysis chamber, which contains pre-filled conversion reagents (bisulfite), the reaction temperature is immediately raised to at least 40° C. or even to around 50 to 60° C. in the lysis chamber for 1 hour to produce a lysate and to deaminate the cytosine base in the nucleic acid in said patient sample (to perform bisulfite conversion of the DNA in said patient sample). It is understood by the person skilled in the art that several steps of the invention may be performed in another order, for example the binding buffer may be added to the nucleic acid after, simultaneously or before adding the bisulfite reagent to the nucleic acid.

The required volume of the conversion reagent depends on the volume of the lysis chamber. In a particular embodiment, a volume of 700 µl of the conversion reagent (e.g. bisulfite reagent) is used in the lysis chamber to ensure that the pumping of the fluids in the automated system works properly. In the Zymo Research EZ DNA Methylation-Lightning™ Kit which is currently available on the market, a volume of 130 µl of the conversion reagent for 20 µl of a DNA sample is used. So according to a specific embodiment of the current invention, the volume of the conversion reagent is, compared to the kit, increased to 700 µl to fill the lysis chamber in the automated system sufficiently to enable proper working of the pumping systems in the cartridge. Alternatively, other (higher) amounts of volumes of the conversion reagent may be added to the sample in the lysis chamber as required (depending on the sample used), for example 700 µl, 800 µl, 900 µl, 1 ml, 1100 µl, 1200 µl, 1300 µl, 1400 µl, 1500 µl, 1600 µl, 1700 µl, 1800 µl, 1900 µl, 2 ml, 2100 µl, 2200 µl, 2300 µl, 2400 µl, 2500 µl, 2600 µl, 2700 µl, 2800 µl, 2900 µl or 3 ml bisulfite reagents can be added to the sample introduced into the automated system, to perform bisulfite conversion of the nucleic acid/DNA according to the methods of the present invention.

In another embodiment, the present invention is directed to a kit for performing a bisulfite reaction in an automated system comprising:

- a cartridge according to the invention for use in an automated system, comprising bisulfite, binding buffer and desulphonation buffer, and
- instructions for use.

In yet another embodiment, the present invention provides a kit for performing a bisulfite reaction in an automated system comprising:

- a cartridge according to the invention for use in an automated system, comprising an extraction chamber comprising an extraction membrane, bisulfite, binding buffer and desulphonation buffer, and
- instructions for use.

Preferably the methods, cartridges and kits according to the invention are used in diagnostics, for example for the screening of tissue or fluids from the human or even animal body for the presence of certain methylation patterns, e.g. to predict the risk of development of a cell proliferative disorder. The methods, the detection systems, the cartridges and the kits of the invention, and uses thereof, can be practised for screening, early detection, disease progression and predicting outcome of therapy response in cancer.

Clauses

Clause 1. A method for a detection of a nucleic acid methylation status in an automated system comprising an extraction chamber comprising an extraction membrane, said method comprising the steps of:

introducing a source of the nucleic acid into the automated system, adding bisulfite to the nucleic acid and immediately followed by heating the source of the nucleic acid to a temperature between 40° C. and 80° C. to produce a lysate comprising the nucleic acid and to deaminate an unmethylated cytosine base present in said nucleic acid;

adding binding buffer to the lysate to produce a binding buffer-and-lysate-solution;

binding the nucleic acid to the extraction membrane and removing the bisulfite by controlled pumping of the binding buffer-and-lysate-solution over the extraction membrane;

adding desulphonation buffer to the extraction chamber and controlled pumping of the desulphonation buffer over the extraction membrane to desulphonate the base deaminated in a previous step in the nucleic acid and to convert said base to an uracil base, eluting the converted nucleic acid from the extraction membrane; and analyzing the converted nucleic acid in the automated system.

Clause 2. A method for a detection of a nucleic acid methylation status in an automated system comprising an extraction chamber comprising an extraction membrane according to clause 1, said method comprising the subsequent steps of:

a) introducing a source of the nucleic acid into the automated system, adding bisulfite to the nucleic acid and immediately followed by heating the source of the nucleic acid to a temperature between 40° C. and 80° C. to produce a lysate comprising the nucleic acid and to deaminate an unmethylated cytosine base present in said nucleic acid;

b) adding binding buffer to the lysate to produce a binding buffer-and-lysate-solution;

c) binding the nucleic acid to the extraction membrane and removing the bisulfite by controlled pumping of the binding buffer-and-lysate-solution over the extraction d) adding desulphonation buffer to the extraction chamber and controlled pumping of the desulphonation buffer over the extraction membrane to desulphonate the base deaminated in step a) in the nucleic acid and to convert said base to an uracil base, e) eluting the converted nucleic acid from the extraction membrane; and analyzing the converted nucleic acid in the automated system.

Clause 3. Method according to clause 1 or 2, wherein the immediate heating of the source of the nucleic acid is at a temperature between 40° C. and 60° C., and/or the controlled pumping is performed with a flow rate slower than or equal to 0.1 ml/s.

Clause 4. Method according to any one of clauses 1 to 3, wherein the flow rate in step c) and the flow rate in step d) is comprised between 0.001 ml/s and 0.1 ml/s.

Clause 5. Method according to any one of clauses 1 to 4, wherein at least one of the flow rate in step c) and the flow rate in step d) is between 0.001 and 0.0017 ml/s.

Clause 6. Method according to any one of clauses 1 to 5, wherein the flow rate in step d) is slower than the flow rate in step c).

Clause 7. Method according to any one of clauses 1 to 6, characterized in that the nucleic acid analysis comprises nucleic acid amplification.

Clause 8. Method according to any one of clauses 1 to 7, wherein detection of the presence or absence of a methylated cytosine base in the nucleic acid is indicative of a cell proliferative disorder.

Clause 9. Method according to any one of clauses 1 to 8, wherein the nucleic acid source is a human tissue sample.

Clause 10. Method according to any one of clauses 1 to 9, wherein the extraction membrane is a silica membrane, or a composite membrane comprising 2 or 3 silica membrane layers.

Clause 11. Use of a cartridge for detection of a nucleic acid methylation status according to the method of any one of clauses 1 to 10.

Clause 12. Use of a cartridge according to clause 11, said cartridge comprising an extraction chamber comprising an extraction membrane.

Clause 13. Use of a cartridge according to clauses 11 or 12, characterized in that the cartridge comprises a lysis chamber wherein steps a) to b) of the method according to any of clauses 1 to 10 are performed, and an extraction chamber wherein steps c) to e) of the method according to clauses 1 to 10 are performed, wherein there is a channel between the lysis chamber and the extraction chamber for transporting fluids from the lysis chamber to the extraction chamber.

Clause 14. Use of an automated system for a detection of a nucleic acid methylation status in a source of a nucleic acid, the automated system adapted for receiving a cartridge as defined in any of clauses 11 to 13, the system controlling the steps of:

a) adding bisulfite to a source of a nucleic acid introduced into the system and immediately followed by heating the source of the nucleic acid to a temperature between 40° C. and 80° C. to produce a lysate comprising the nucleic acid and to deaminate an unmethylated cytosine base present in said nucleic acid, b) adding binding buffer to the lysate comprising nucleic acid to produce a binding buffer-and-lysate-solution, c) binding the nucleic acid to the extraction membrane and removing the bisulfite by controlled pumping of the binding buffer-and-lysate-solution over the extraction membrane, d) adding desulphonation buffer to the extraction chamber and controlled pumping of the desulphonation buffer over the extraction membrane to desulphonate the base deaminated in step a) in the nucleic acid and to convert said base to an uracil base, e) eluting the converted nucleic acid from the extraction membrane, and f) analyzing the converted nucleic acid.

Clause 15. Use of a system according to clause 14, wherein the immediate heating of the source of the nucleic acid is at a temperature between 40° C. and 60° C., and/or wherein the controlled pumping is performed with a flow rate slower than or equal to 0.1 ml/s.

Clause 16. Use of a system according to clause 14 or 15, wherein the nucleic acid source is a human tissue sample.

Clause 17. A kit for performing a bisulfite reaction in an automated system comprising:
  g) a cartridge as defined in any of clauses 11 to 13 for use in an automated system, comprising bisulfite, binding buffer and desulphonation buffer, and
  h) instructions for use.

The following examples are provided to aid the understanding of the present invention, the true scope of which is set forth in the appended claims.

EXAMPLES

Example 1. Performing Bisulfite Conversion of Spiked DNA Samples in an Idylla™ Cartridge Using the Idylla™ System The different containers of an open Idylla™ cartridge (including an extraction membrane) were filled with the buffers of the EZ DNA Methylation Lightning Kit of ZymoResearch (Cat. No D5031). Container 1 of the cartridge contained 2 ml of the lightning conversion reagent. Container 2 contained 2.5 ml of M-binding buffer. In container 3 and 4 there was 2 ml of M-wash buffer added. Before using the wash buffer by ZymoResearch we made sure that there was 24 ml of 100% ethanol added to the 6 ml of wash buffer concentrate. Container 5 of the cartridge contained 1.5 ml of L-desulphonation buffer and container 6 contained 1.5 ml of the elution buffer, which in this case is ultrapure water. 5 µl of the un-methylated DNA (provided from ZymoResearch Cat. No D5014-1) and methylated DNA (provided by Millipore Cat. NoS 7821) were spiked in the lysis chamber of the Idylla™ cartridge. When performing the bisulfite conversion protocol on the Idylla™ system, 700 µl of the conversion reagent was pumped to the lysis chamber. In the lysis chamber the temperature was raised to at least 40° C. by heating the peltier. Setting of the wall temperature on 40° C. means that the real temperature inside the lysis chamber of the cartridge will be around 50° C. The DNA and conversion reagents were incubated in the lysis chamber on 40° C. (wall temperature) for 1 hour. After incubation, 2 ml of the M-binding buffer (container 2) was pumped to the lysis chamber. All content of the lysis chamber was pumped over the extraction membrane with a flowrate of 0.1 ml/s. Then the first wash step was executed, by pumping 3 times 0.2 ml of M-wash buffer out of container 3 over the extraction membrane with temperature of 40° C. After the wash step the L-desulphonation step took place, by pumping 0.9 ml (2 times 0.45 ml) L-desulphonation buffer with a flowrate of 0.0017 ml/s over the extraction membrane with a temperature of 20° C. This L-desulphonation step takes around 9 minutes. The last wash step was performed by pumping 7 times 0.3 ml wash buffer (total of 2.1 ml) of container 4 over the extraction membrane with a flowrate of 0.1 ml/s. After this last wash step, ethanol evaporation was performed by pumping 20 ml of air (using air inlet) with a flowrate of 0.1 ml/s over the membrane (temperature of the membrane is 110° C.). Elution of the DNA to the mix chamber was performed by adding 0.25 ml of elution buffer (container 6) over the membrane with a flowrate of 0.1 ml/s.

Figure 1A:
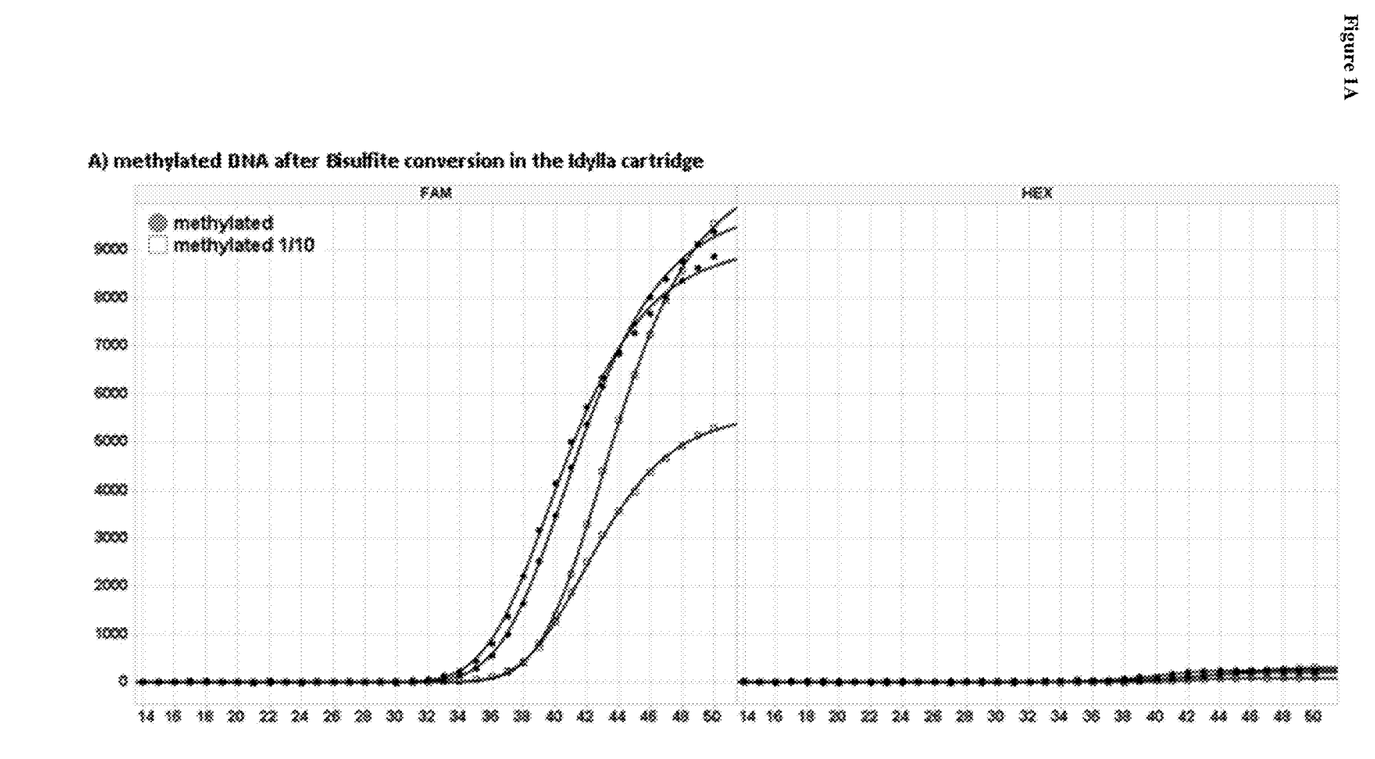
FIG. 1: Graph demonstrating PCR amplification results of A) methylated DNA after bisulfite conversion and B) un-methylated DNA after bisulfite conversion in the cartridge. Converted un-methylated DNA gives a HEX signal due to the fact that the un-methylated specific probe has a VIC fluorophore added. Converted methylated DNA gives a PCR with a FAM signal, because of the fact that the methylated specific probe has a FAM fluorophore added.
Figure 1B:
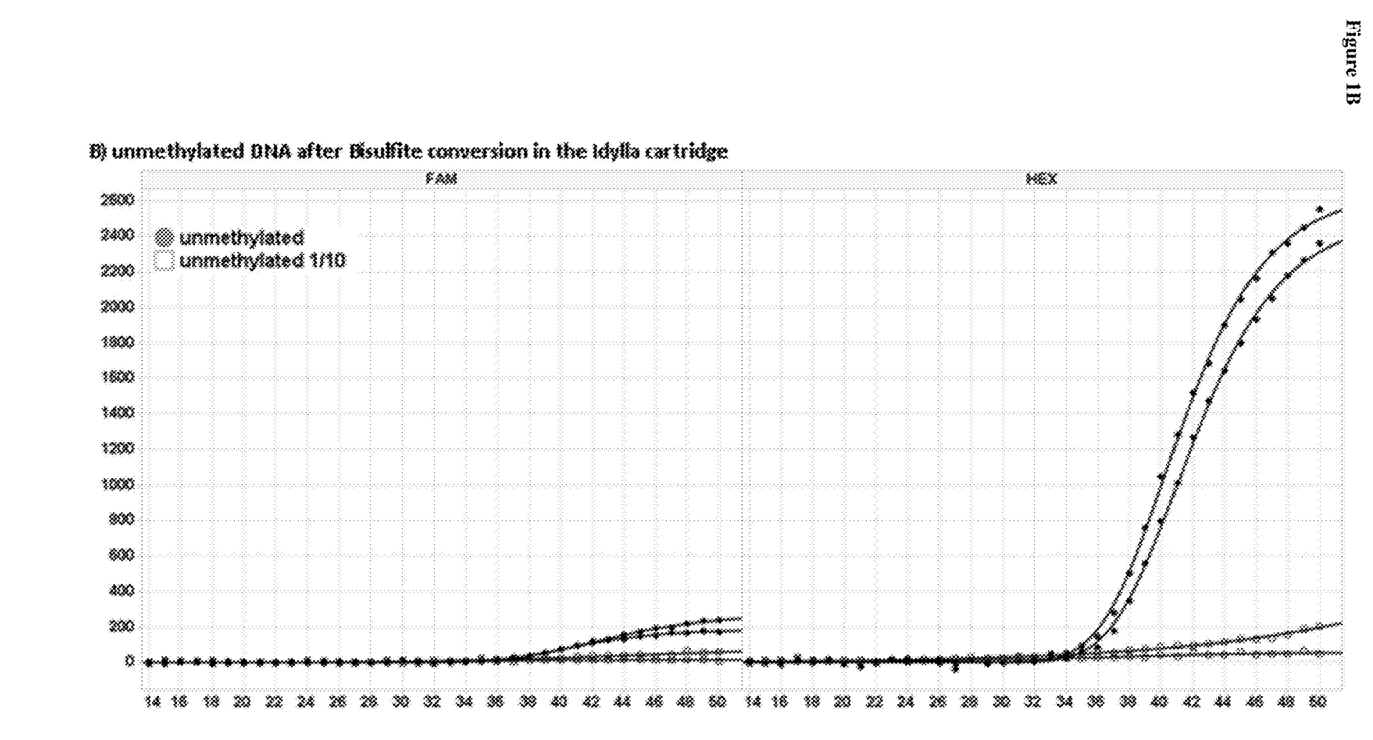

Example 2. Checking Bisulfite Conversion by Real Time-PCR (RT-PCR) and Sequencing 5 µl of the obtained elutions were analyzed in a 25 µl RT-PCR reaction using a bisulfite converted specific assay provided by Qiagen (the EpitectMethyLight Assay: Hs_ONECUT2.) and this according to the manufacturer's instructions. FIG. 1 indicates the results of the real time PCR for both un-methylated and methylated converted DNA. The un-methylated converted DNA shows a PCR amplification with a HEX signal on Biorad (VIC—probe in the Qiagen kit to detect un-methylated bisulfite converted DNA). The methylated converted DNA shows a good PCR amplification with a FAM signal on Biorad (FAM probe—in the Qiagen kit to detect methylated bisulfite converted DNA). If there had been no conversion present in the Idylla™ cartridge there would not be a PCR result, because of the fact that the Qiagen assay is an assay specific for bisulfite converted DNA. Primers and probe would not bind to un-converted DNA.

Figure 2:
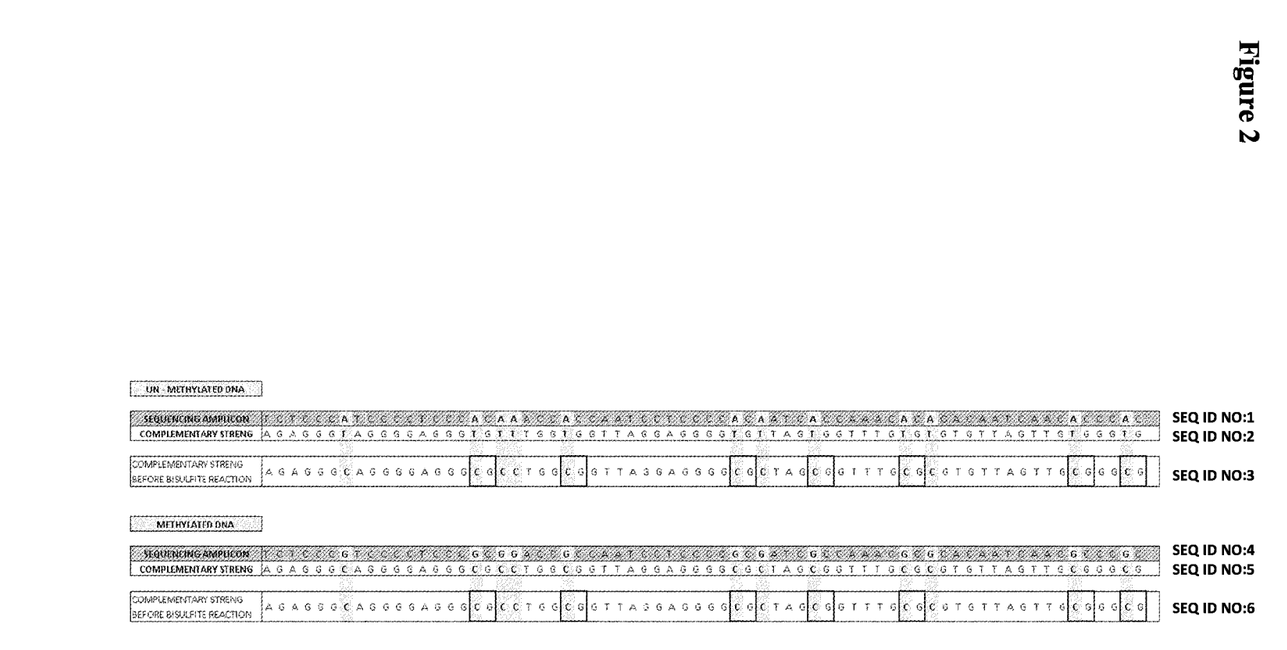
FIG. 2: Visual representation of sequencing results of the amplicon of un-methylated and methylated converted DNA. Part of the sequencing amplicon is indicated in grey. First sequence is of the un-methylated DNA; all cytosines are un-methylated and will change to a thymine during bisulfite conversion. Note that the complementary strand of the amplicon after conversion is complementary to the sequence of the amplicon. For the methylated converted DNA, knowing that all cytosines are methylated and will not be changed by bisulfite conversion, the complementary strand before bisulfite reaction is the same as after the reaction.

Also the amplicons provided after RT-PCR were sequenced to investigate the conversion of the un-methylated cytosines in comparison of the methylated cytosines. As shown in FIG. 2, all the un-methylated cytosines from the un-methylated DNA were converted to thymines and detected in the sequence of the amplicon as an adenine.

Example 3. Performing Bisulfite Conversion of a FFPE Tissue Sample in an Idylla™ Cartridge Using the Idylla™ System The different containers of an Idylla™ cartridge (including an extraction membrane) are filled with the buffers of the EZ DNA Methylation Lightning Kit of ZymoResearch (Cat. No D5031). Container 1 of the cartridge contains 3 ml of the lightning conversion reagent. Container 2 contains 2.5 ml of M-binding buffer. Container 3 and 4 each contain 2 ml of M-wash buffer. Before using the wash buffer by ZymoResearch we make sure that there is 24 ml of 100% ethanol added to the 6 ml of wash buffer concentrate. Container 5 of the cartridge contains 1.5 ml of L-desulphonation buffer and container 6 contains 1.5 ml of the elution buffer, which in this case is ultrapure water. A formalin fixed paraffin embedded tissue cancer sample (which comprises human cancer cells) from a patient having colorectal cancer is inserted via the introduction aperture into the lysis chamber of an Idylla™ cartridge. First liquefaction of the FFPE sample is performed with a Biocartis' proprietary buffer in the lysis chamber (sample preparation). For performing the bisulfite conversion protocol on the Idylla™ system, 3 ml of the conversion reagent is pumped to the lysis chamber. The reaction temperature inside the lysis chamber is raised to a temperature between 50° C. and 55° C. by heating the peltier, and the DNA (from the FFPE sample) and conversion reagent are incubated in the lysis chamber for 1 hour. After incubation, 2 ml of the M-binding buffer (container 2) is pumped to the lysis chamber. All content of the lysis chamber is pumped over the extraction membrane with a flowrate of 0.0017 ml/s. Then the first wash step is executed, by pumping 3 times 0.2 ml of M-wash buffer out of container 3 over the extraction membrane with a temperature of 40° C. After the wash step the L-desulphonation step takes place, by pumping 0.9 ml (2 times 0.45 ml) L-desulphonation buffer with a flowrate of 0.0017 ml/s over the extraction membrane with a temperature of 20° C. This L-desulphonation step takes around 9 minutes. The last wash step is performed by pumping 7 times 0.3 ml wash buffer (total of 2.1 ml) of container 4 over the extraction membrane with a flowrate of 0.1 ml/s. After this last wash step, ethanol evaporation is performed by pumping 20 ml of air (using air inlet) with a flowrate of 0.1 ml/s over the membrane (temperature of the membrane is 110° C.). Elution of the DNA to the mix chamber is performed by adding 0.25 ml of elution buffer (container 6) over the membrane with a flowrate of 0.1 ml/s.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

The invention claimed is:

1. A method for detecting nucleic acid methylation status in an automated system comprising an extraction chamber comprising an extraction membrane, said method comprising the steps of:
   a) introducing a source of the nucleic acid into the automated system, wherein the source of the nucleic acid is a biological sample comprising nucleic acids or cells comprising DNA, adding bisulfite to the source of the nucleic acid and immediately followed by heating the source of the nucleic acid to produce a lysate comprising the nucleic acid and to deaminate an unmethylated cytosine base present in said nucleic acid;
   b) adding binding buffer to the lysate to produce a binding buffer-and-lysate-solution;
   c) binding the nucleic acid to the extraction membrane and removing the bisulfite by transporting the binding buffer-and-lysate-solution over the extraction membrane by controlled pumping;
   d) adding desulphonation buffer to the extraction chamber and transporting the desulphonation buffer over the extraction membrane by controlled pumping to desulphonate the base deaminated in a previous step in the nucleic acid and to convert said base to an uracil base; and
   e) eluting the converted nucleic acid from the extraction membrane; and
   f) analyzing the converted nucleic acid wherein the transporting by controlled pumping in step d) is slower than the transporting by controlled pumping in step c).

2. The method according to claim 1, wherein the heating of the source of the nucleic acid is performed at a temperature between about 40° C. and about 80° C.

3. The method according to claim 1, wherein the analysis of the converted nucleic acid is performed in said automated system.

4. The method according to claim 1, wherein the heating of the source of the nucleic acid is performed at a temperature between 40° C. and 60° C.

5. The method according to claim 1, wherein the transporting by controlled pumping in step c) and the transporting by controlled pumping in step d) are at a flow rate between 0.001 ml/s and 0.1 ml/s.

6. The method according to claim 1, wherein the extraction membrane is a silica membrane, or a composite membrane comprising 2 or 3 silica membrane layers.

7. The method according to claim 1, wherein the controlled pumping in step c) and step d) is performed at a flow rate slower than or equal to 0.1 ml/s.

* * * * *

UNITED STATES PATENT AND TRADEMARK OFFICE
CERTIFICATE OF CORRECTION

Page 1 of 1

PATENT NO. : 10,533,210 B2
APPLICATION NO. : 15/570946
DATED : January 14, 2020
INVENTOR(S) : David Nauwelaers et al.

It is certified that error appears in the above-identified patent and that said Letters Patent is hereby corrected as shown below:

On the Title Page

Item (54), "DETECTION OF METHYLATED DNA" should be --IMPROVED DETECTION OF METHYLATED DNA--.

In the Specification

Column 1, Line 1, "DETECTION OF METHYLATED DNA" should be --IMPROVED DETECTION OF METHYLATED DNA--.

Column 23, Line 51, "extraction" should be --extraction membrane--.

Signed and Sealed this
Thirty-first Day of March, 2020

Andrei Iancu
*Director of the United States Patent and Trademark Office*